US008933115B2

(12) United States Patent
Pavliv et al.

(10) Patent No.: US 8,933,115 B2
(45) Date of Patent: Jan. 13, 2015

(54) STABILIZED STATIN FORMULATIONS (71) Applicant: Cumberland Pharmaceuticals Inc., Nashville, TN (US)

(72) Inventors: Leo Pavliv, Cary, NC (US); Andrew Vila, Nashville, TN (US)

(73) Assignee: Cumberland Pharmaceuticals Inc., Nashville, TN (US)

( * ) Notice: Subject to any disclaimer, the term of this patent is extended or adjusted under 35 U.S.C. 154(b) by 0 days.

(21) Appl. No.: 13/746,999

(22) Filed: Jan. 22, 2013

(65) Prior Publication Data

US 2013/0137745 A1 May 30, 2013

Related U.S. Application Data (63) Continuation of application No. 12/762,025, filed on Apr. 16, 2010.

(51) Int. Cl.
*A61K 31/724* (2006.01)
*A61K 31/40* (2006.01)
*C07D 207/34* (2006.01)
*A61K 47/40* (2006.01)
*A61K 9/00* (2006.01)
*A61K 9/19* (2006.01)

(52) U.S. Cl.
CPC ............ *A61K 47/40* (2013.01); *A61K 9/0019* (2013.01); *A61K 9/19* (2013.01); *A61K 31/40* (2013.01)
USPC ................ 514/423; 514/58; 514/54; 548/537

(58) Field of Classification Search
None
See application file for complete search history.

(56) References Cited

U.S. PATENT DOCUMENTS

| | | | |
|---|---|---|---|
| 4,231,938 A | 11/1980 | Monaghan et al. | |
| 4,346,227 A | 8/1982 | Terahara et al. | |
| 4,444,784 A | 4/1984 | Hoffman et al. | |
| 4,588,715 A | 5/1986 | Damon, II | |
| 4,613,610 A | 9/1986 | Wareing | |
| 4,739,073 A | 4/1988 | Kathawala | |
| 4,751,235 A | 6/1988 | Anderson | |
| 4,755,606 A | 7/1988 | Wareing | |
| 4,804,679 A | 2/1989 | Anderson | |
| 4,808,607 A | 2/1989 | Wareing | |
| 4,822,799 A | 4/1989 | Kathawala | |
| 4,829,081 A | 5/1989 | Damon, II et al. | |
| 4,851,427 A | 7/1989 | Wareing | |
| 4,868,185 A | 9/1989 | Chucholowski et al. | |
| 4,876,280 A | 10/1989 | Damon, II | |
| 4,927,851 A | 5/1990 | Damon, II et al. | |
| 4,939,159 A | 7/1990 | Anderson et al. | |
| 4,946,841 A | 8/1990 | Baader et al. | |
| 5,001,255 A | 3/1991 | Kathawala | |
| 5,013,749 A | 5/1991 | Watson et al. | |
| 5,026,708 A | 6/1991 | Fujikawa et al. | |
| 5,177,080 A | 1/1993 | Angerbauer et al. | |
| 5,260,440 A | 11/1993 | Hirai et al. | |
| 5,273,995 A | 12/1993 | Roth | |
| 5,354,772 A | 10/1994 | Kathawala | |
| 5,356,896 A | 10/1994 | Kabadi et al. | |
| 6,566,347 B1 | 5/2003 | Adeyeye et al. | |
| 6,610,671 B2 | 8/2003 | Buchanan | |
| 6,699,849 B1 * | 3/2004 | Loftsson et al. ................. 514/58 |
| 7,939,675 B2 | 5/2011 | Debetten-Court et al. | |
| 2004/0247673 A1 * | 12/2004 | Fergione et al. .............. 424/469 |
| 2005/0215520 A1 * | 9/2005 | Liu et al. .......................... 514/58 |
| 2008/0269314 A1 | 10/2008 | Debetten-Court et al. | |
| 2009/0247603 A1 * | 10/2009 | Joshi .............................. 514/423 |
| 2011/0257240 A1 | 10/2011 | Pavliv et al. | |

FOREIGN PATENT DOCUMENTS

| | | |
|---|---|---|
| CA | 2684560 A1 | 10/2008 |
| CN | 101658677 A | 3/2010 |
| CN | 101658677 A * | 3/2010 |
| EP | 304063 A2 | 2/1989 |
| EP | 324347 A2 | 7/1989 |
| EP | 367895 A1 | 5/1990 |
| EP | 1514877 A1 * | 3/2005 |
| EP | 1891943 A2 | 2/2008 |
| JP | 2005-530866 | 10/2005 |
| WO | WO 97/23200 | 7/1997 |
| WO | WO 0035425 A1 * | 6/2000 |
| WO | WO 03/068191 A1 | 8/2003 |
| WO | WO 2008/032327 A2 | 3/2008 |

OTHER PUBLICATIONS

Background for the Dec. 17, 2002 Carcinogen Identification Committee Meeting Agenda Item: Consideration of Request to Review Statin Drugs as a Group for Subsequent Listing Consideration [Nov. 14, 2002], available at http://oehha.ca.gov/prop65/public_meetings/statinback.html. (last visited on May 15, 2012).*
Definition of "slurry". See http://www.merriam-webster.com/dictionary/slurry, available on Jan. 14, 2014.*
Office Action dated Mar. 11, 2014 for the corresponding Japanese Patent Application No. 2013-504949.*
Patel, RP et al., Solid-State Characterization and Dissolution Properties of Lovastatin Hydroxypropyl-b-Cyclodextrin Inclusion Complex, Pharmaceutical Technology, 2007, vol. 31, No. 2, p. 72-74 and 76-82.*
Armstrong et al., Separation of Drug Stereoisomers by the Formation of b-Cyclodextrin Inclusion Complexes, Science, vol. 232, p. 1132-1135, May 30, 1986.*
Cyclobond® Handbook, A Guide to Using Cyclodextrin Bonded Phases for Chiral LC Separations, 6th ed., © 2002 Advanced Separation Technologies, Inc., p. 1-58, at p. 42-45.*
Background for the Dec. 17, 2002 Carcinogen Identification Committee Meeting Agenda Item: Consideration of Request to Review Statin Drugs as a Group for Subsequent Listing Consideration [Nov. 14, 2002], available at http://oehha.ca.gov/prop65/public_meetings/statinback.html. (last visited on Sep. 30, 2014).*

(Continued)

*Primary Examiner* — Svetlana M Ivanova
(74) *Attorney, Agent, or Firm* — Davidson, Davidson & Kappel, LLC (57) ABSTRACT

The present invention is directed to statin formulations having improved solubility and/or stability and methods for the same.

27 Claims, 1 Drawing Sheet

(56) References Cited

OTHER PUBLICATIONS

International Search report, dated Jun. 1, 2011, issued in connection with corresponding International Application PCT/US 11/31388.

Süle et al. "Enhancement of Drug Solubility in Supramolecular and Colloidal Systems." Journal of Pharmaceutical Sciences, vol. 98, No. 2, pp. 484-494; 2009.

Patel et al. "Physico-Chemical Characterization and In Vitro Dissolution Behavior of Simvastatincyclodextrin Inclusion Compounds." Drug Delivery Technology, vol. 7, No. 5, pp. 50-56; 2007.

Background for the Dec. 17, 2002 Carcinogen Identification Committee Meeting Agenda Item: Consideration of Request to Review Statin Drugs as a Group for Subsequent Listing Consideration [Nov. 14, 2002], available at http://oehha.ca.gov/prop65/public_meetings/statinback.html.

European Search report, dated Nov. 14, 2013, issued in connection with corresponding European Application EP 11769321.

Patel, RP, et al. "Solid-State Characterization and Dissolution Properties of Lovastatin Hydroxypropyl-β-Cyclodextrin Inclusion Complex", Pharmaceutical Technology, 2007, vol. 31, No. 2, p. 72-74 and 76-82.

* cited by examiner

STABILIZED STATIN FORMULATIONS

This application is a continuation of U.S. patent application Ser. No. 12/762,025, filed Apr. 16, 2010.

BACKGROUND OF THE INVENTION

It has been clear for several decades that elevated blood cholesterol is a major risk factor for coronary heart disease (CHD), and many studies have shown that the risk of CHD events can be reduced by lipid-lowering therapy. Prior to 1987, the lipid-lowering armamentarium was limited essentially to diet modification to a low saturated fat and cholesterol diet, the bile acid sequestrants (cholestyramine and colestipol), nicotinic acid (niacin), the fibrates and probucol. Unfortunately, all of these treatments have limited efficacy or tolerability, or both. With the introduction of lovastatin (MEVACOR®; see U.S. Pat. No. 4,231,938)—the first inhibitor of HMG-CoA reductase to become available for prescription in 1987—physicians for the first time were able to obtain comparatively large reductions in plasma cholesterol with very few adverse effects.

The HMG CoA reductase inhibitors, commonly known are statins, are divided into two groups: fermentation-derived and synthetic. In addition to the natural product lovastatin, there have been several semi-synthetic and totally synthetic HMG-CoA reductase inhibitors approved for prescription use, including simvastatin (ZOCOR®; see U.S. Pat. No. 4,444,784), pravastatin sodium salt (PRAVACHOL®; see U.S. Pat. No. 4,346,227), fluvastatin sodium salt (LESCOL®; see U.S. Pat. No. 5,354,772), atorvastatin calcium salt (LIPITOR®; see U.S. Pat. No. 5,273,995) and cerivastatin sodium salt (BAYCOL®; see U.S. Pat. No. 5,177,080). Still other HMG-CoA reductase inhibitors are known to be in development, for example pitavastatin also referred to as NK-104 (see PCT international publication number WO 97/23200); and rosuvastatin also known as ZD-4522 (CRESTOR®; see U.S. Pat. No. 5,260,440, and Drugs of the Future, 1999, 24(5), pp. 511-513). The structural formulas of these and additional HMG-CoA reductase inhibitors, are described at page 87 of M. Yalpani, "Cholesterol Lowering Drugs", Chemistry & Industry, pp. 85-89 (5 Feb. 1996). The HMG-CoA reductase inhibitors described above belong to a structural class of compounds which contain a moiety which can exist as either a 3-hydroxy lactone ring or as the corresponding ring opened dihydroxy open-acid, and are often referred to as "statins."

U.S. Pat. No. 5,356,896 describes a pharmaceutical dosage form comprising an HMG-CoA reductase inhibitor compound, e.g., fluvastatin sodium, which is stabilized against pH-related degradation by an alkaline stabilizing medium capable of imparting a pH of at least 8 to an aqueous solution or dispersion of the composition. The '896 patent states that the drug substance and the alkaline medium must be brought into intimate contacting association, preferably with an aqueous or other solvent-based preparative process, whereby "the drug substance and alkaline medium are blended together in the presence of minor amounts of, e.g., water, to provide particles containing the drug and alkaline substance in intimate admixture." The resulting particles are dried and then are blended with filler and remaining excipients, which were set aside to comprise an "external phase" of said particles, to result in a composition suitable for encapsulation, tableting or the like.

In another embodiment described in the '896 patent, a solvent-based process is utilized to assist subsequent drying in a fluidized bed, whereby the drug substance and alkaline medium are wet granulated by known techniques, i.e. blended in the moistened state, together with an amount of the filler material and the resulting granules, after drying, are combined with any remaining filler and other set-asides, e.g., binder, lubricant, and can therefore be tableted, encapsulated, or otherwise shaped into a dosage form.

The '896 patent states that to achieve extended shelf life of the compositions, it is important "that the particles prepared by trituration or wet granulation or other aqueous-based process be substantially completely dried, i.e. to a weight loss on drying (L.O.D.) of not greater than 3%, and preferably not greater than 2%." The '896 patent also describes conventionally performed drying by tray drying or in a fluidized bed, preferably the latter with drying typically performed at about 50.degree C. inlet temperature, and below 50% RH. The '896 patent additionally describes an alternative preparative procedure to the above-described trituration or wet granulation techniques, wherein the drug substance and the alkaline stabilizing medium can be co-lyophilized, i.e. freeze-dried, from aqueous solution as a step in situ of the drug manufacturing process.

Most statins are relatively insoluble, and are considered by those skilled in the art to be unstable in solution, and therefore this class of drugs is manufactured in solid form. However, there are those patients who can not ingest, digest, or otherwise take medications orally and there is a need for the administration of medications intravenously. There are clinical indications that statins through anti-inflammatory and possibly other mechanisms can reduce the incidence of heart attacks, strokes, as well as other inflammatory mediated conditions.

SUMMARY OF THE INVENTION

It is an object of the invention to provide a stable product containing a statin that can be administered intravenously.

It is further object of the invention to provide a solid statin formulation which may be reconstituted in an aqueous solution suitable for injection into mammals.

It is another object of the invention to provide lyophilized particles of a statin and a solubilizing or complexing agent.

It is a further object to provide a method of preparing lyophilized particles of a statin and a solubilizing or complexing agent.

It is a further object to provide a method of treating human patients with a statin using the formulations and methods described herein.

These objects and others are achieved by the present invention, which is related in part to a water-insoluble statin complexed with a sufficient amount of a pharmaceutically acceptable complexing agent in a solution having a pH of from about 7 to about 9 to provide a solubilized statin concentration of at least about 3.32 mg/ml. The invention is further related to a pharmaceutical formulation comprising an effective amount of the complexed statin as described above.

In certain embodiments, the solubilized statin concentration is from about 1 mg/ml to about 25 mg/ml. In certain preferred embodiments, the solubilzed statin concentration is from about 5 mg/ml to about 15 mg/ml. In certain preferred embodiments, the solubilized statin concentration is about 10 mg/ml.

In some embodiments, the statin may be selected from lovastatin, simvastatin, mevastatin, atorvastatin, cerivastatin and rivastatin.

In some embodiments, the complexing agent is a cyclodextrin. In certain preferred embodiments, the complexing agent is hydroxy-propyl-β-cyclodextrin.

In some embodiments, the complexed statin is lyophilized.

The invention is also directed in part to solid particles comprising a water-insoluble statin which may be readily solubilized in an aqueous solution suitable for injection into mammals, which are lyophilized particles comprising a pharmaceutically acceptable statin and a sufficient amount of a pharmaceutically acceptable complexing agent.

The invention is further directed in part to lyophilized particles comprising a water-insoluble statin and an effective amount of a complexing agent to provide aqueous solubility to said statin and to provide stability to the formulation when reconstituted in an aqueous environment.

In certain embodiments, the lyophilized particles are prepared by first adding the water-insoluble statin to a complexing agent, after which the combination is mixed. In some embodiments, the formulation is then lyophilized to obtain lyophilized particles.

In certain preferred embodiments of the invention, the lyophilized particles comprising the water-insoluble statin and complexing agent are stable. By "stable", it is meant that substantially no degradation of the lyophilized particles (the product) is observed after storage for 1 month at 40° C. In preferred embodiments, the term "stable" with respect to the lyophilized particles comprising the water-insoluble statin and complexing agent means that there is less than about 0.1% degradation observed) after storage for 1 month at 40° C.

In some embodiments of the present invention, the pH is adjusted to from about 7 to about 9 using a pharmaceutically acceptable buffer or alkalizing agent, with suitable alkalizing agents and buffers including but not limited to NaOH, KOH, triethylamine, meglumine, L-Arginine, sodium phosphate buffer (either sodium phosphate tribasic, sodium phosphate dibasic, sodium phosphate monobasic, or o-phosphoric acid), sodium bicarbonate, and mixtures of any of the foregoing. In an embodiment of the invention, the lyophilized particles contain one of the following statins: lovastatin, simvastatin, pravastatin, mevastatin, fluvastatin, atorvastatin, rosuvastatin, cerivastatin and rivastatin. The lyophilized particles in certain embodiments may contain a cyclodextrin as the complexing agent and in certain preferred embodiments, the cyclodextrin is hydroxy-propyl-β-cyclodextrin.

The invention is also directed in part to a method of preparing lyophilized particles comprising a pharmaceutically acceptable statin and a pharmaceutically acceptable complexing agent wherein the statin is added to a mixture of the complexing agent and a suitable solvent after which the combination is mixed. In certain embodiments, the pH is then adjusted using a pharmaceutically acceptable buffer to a pH range of from about 7 to about 9. The mixture may then be lyophilized to obtain lyophilized particles. The pharmaceutically acceptable statin is preferably water-insoluble, and may be selected, e.g., from the group consisting of lovastatin, simvastatin, mevastatin, atorvastatin, cerivastatin and rivastatin. In certain embodiments, the complexing agent is a cyclodextrin.

Although in certain preferred embodiments the invention contemplates the use of a statin that is water-insoluble, in further embodiments of the invention the statin may be water insoluble or water soluble. Examples of suitable water soluble statins include, but are not limited to, risuvastatin, fluvastatin and pravastatin.

Thus, in certain embodiments, the invention is directed to stable formulations of a soluble statin and methods for preparing the same. In such embodiments, the soluble statin(s) is stabilized via a lyophilization step as described herein.

The invention is also directed to a method of preparing a stable pharmaceutical formulation comprising lyophilized particles of statin, wherein the statin is complexed with an effective amount of a pharmaceutically acceptable complexing agent in an aqueous solution and the pH is adjusted to from about 7 to about 9 prior to lyophilization.

In certain embodiments, the lyophilized particles are reconstituted in an effective amount of a pharmaceutically acceptable solution for injection into a human patient. In certain further embodiments, the reconstituted lyophilized particles are injected into a human patient The present invention is also directed in part to a method of treatment comprising (a) preparing lyophilized particles by adding a statin to a mixture of a complexing agent and a suitable solvent and lyophilizing the mixture to obtain lyophilized particles; (b) reconstituting the lyophilized particles in a pharmaceutically acceptable solution for injection; and (c) administering a suitable quantity of the solution to provide an effective amount of statin to a human patient in need of treatment. In certain embodiments, the statin is administered in an effective amount to lower the patient's lipid level and/or to produce a desired (therapeutically effective) anti-inflammatory effect or other therapeutic effect.

In some embodiments, after the statin is added to the mixture of the complexing agent and the solvent, the mixture is vortexed and sonicated and the pH of the mixture is adjusted to from about 7 to about 9 using a pharmaceutically acceptable buffer.

In certain embodiments, the statin is selected from the group consisting of lovastatin, simvastatin, pravastatin, mevastatin, fluvastatin, atorvastatin, rosuvastatin, cerivastatin and rivastatin and the complexing agent is a cyclodextrin.

In certain embodiments of the present invention, the complexing agent comprises at least about 13.5% of the formulation.

It certain embodiments of the present invention, a solubilized statin concentration of at least about 3.3 mg/ml is provided.

As mentioned above, objects of the present invention also comprise pharmaceutical compositions containing at least a compound of the present invention of formula (I) together with non toxic adjuvants and/or carriers usually employed in the pharmaceutical field.

DETAILED DESCRIPTION OF THE INVENTION

The present invention is directed in part to pharmaceutical formulations comprising an effective amount of a pharmaceutically acceptable statin complexed with a sufficient amount of a pharmaceutically acceptable complexing agent and method for preparing the same.

The present invention is further directed in part to formulations which include a water-insoluble statin which is complexed with a sufficient amount of a pharmaceutically acceptable complexing agent to render the water-insoluble statin soluble in an aqueous environment, which formulation is also lyophilized in order to provide a stable formulation of a water-insoluble statin that can be solubilized in an aqueous environment.

Suitable water insoluble statins for use in the present invention include, but are not limited to, lovastatin, simvastatin, mevastatin, atorvastatin, cerivastatin and rivastatin, pharamaceutically acceptable salts thereof, and pharmaceutically acceptable complexes thereof. The term "water-insoluble" as it is used herein, means the USP definition range of very slightly soluble to insoluble (solubility not more than (NMT) 1:1000). In addition, the present invention is intended to cover compositions comprising other HMG-CoA reductase inhibitor compounds of formula I herein, including both the erythro racemate and its constituent isomers (i.e. the 3R,5S and 3S,5R isomers, preferably the 3R,5S isomer).

(I)

These compounds are disclosed, e.g., in the following commonly assigned patents, published patent applications and publications which are all hereby incorporated herein by reference: U.S. Pat. No. 4,739,073, and EP-A-114,027 (R=indolyl and derivatives thereof); EP-A-367,895 (R=pyrimidinyl and derivatives thereof); U.S. Pat. No. 5,001, 255 (R=indenyl and derivatives thereof); U.S. Pat. No. 4,613, 610 (R=pyrazolyl and derivatives thereof); U.S. Pat. No. 4,851,427 (R=pyrrolyl and derivatives thereof); U.S. Pat. Nos. 4,755,606 and 4,808,607 (R=imidazolyl and derivatives thereof); U.S. Pat. No. 4,751,235 (R=indolizinyl and derivatives thereof); U.S. Pat. No. 4,939,159 (R=azaindolyl and derivatives thereof); U.S. Pat. No. 4,822,799 (R=pyrazolopyridinyl and derivatives thereof); U.S. Pat. No. 4,804,679 (R=naphthyl and derivatives thereof); U.S. Pat. No. 4,876,280 (R=cyclohexyl and derivatives thereof); U.S. Pat. No. 4,829,081 (R=thienyl and derivatives thereof); U.S. Pat. No. 4,927,851 (R=furyl and derivatives thereof); U.S. Pat. No. 4,588,715 (R=phenylsilyl and derivatives thereof); and F. G. Kathawala, Medicinal Research Reviews, Vol. 11 (2), p. 121-146 (1991), and F. G. Kathawala, Atherosclerosis Research—Review, June 1992, p. B73-B85.

Further compounds of formula I are disclosed e.g. in EP-A-304,063 (R=quinolinyl and derivatives thereof); EP-A-330, 057 and U.S. Pat. Nos. 5,026,708 and 4,868,185 (R=pyrimidinyl and derivatives thereof); EP-A-324,347 (R=pyridazinyl and derivatives thereof); EP-A-300,278 (R=pyrrolyl or derivatives thereof); and U.S. Pat. No. 5,013, 749 (R=imidazolyl and derivatives thereof), hereby incorporated by reference.

"Complexing agents" are small molecular weight molecules which can form an inclusion complex and after suitable curing time, can solubilize the drug and may impart additional stability to the drug. Accordingly, for purposes of the present invention, the term "complexing agent" is meant to encompass agents that complex and/or solubilize a water-insoluble statin. In certain embodiments of the present invention, the pharmaceutically acceptable complexing agent is a dextrin. Other suitable dextrins include cyclodextrins such as hydroxy-propyl-β-cyclodextrin and sulfobutyl-ether-β-cyclodextrin. Additional cyclodextrins could include alpha-cyclodextrins, beta-cyclodextrins, gamma-cyclodextrins, beta-cyclodextrin ether comprising one or more hydroxybutyl sulfonate moieties and cyclodextrins as described in U.S. Pat. No. 6,610,671 or U.S. Pat. No. 6,566,347 (both of which are incorporated by reference).

Additional complexing agents include, but are not limited to, the group consisting of phenol, phenolic salts, aromatic acids and esters, carboxylic acids and salts and esters thereof, inorganic acids and bases and amino acids and esters and salts thereof: methylparaben, propylparaben, potassium methylparaben, parabens, ascorbic acid and its derivatives, methyl anthranilate, salicylic acid, acetosalicyclic acid, tocopherol, organic acids, carboxylic acids, aromatic acids, aromatic esters, acid salts of amino acids, benzaldehyde, cnnimaldehyde, imidazole, menthol, thiophenol, m-aminobenzoic acid, anthranilic acid, picolinic acids and alkyl esters thereof, toluidides, sodium benzoate, sodium metabisulphite, malic acid, isoascorbic acid, citric acid, tartaric acid, sodium sulphite, sodium bisulphate, water- and fat-soluble derivatives of tocopherol, sulphites, bisulphites and hydrogen sulphites, propyl/gallate, nordihydroguaiaretic acid, phosphoric acids, sorbic and benzoic acids, methylparaben, sodium methylparaben, para-aminobenzoic acid and esters, sorbic and benzoic acids, 2,6-di-t-butyl-alpha-dimethylamino-p-cresol, t-butylhydroquinone, di-t-amylhydroquinone, di-t-butylhydroquinone, butylhydroxytoluene (BHT), butylhydroxyanisole (BHA), pyrocatechol, pyrogallol, esters, isomeric compounds thereof, pharmaceutically acceptable salts thereof, and mixtures of any of the foregoing.

In certain embodiments of the present invention, the complexing agent comprises at least 13.5% of the formulation.

In certain embodiments, the statin and complexing agent are combined by adding the statin to a mixture of the complexing agent in an aqueous solution. The aqueous solution may be a suitable pharmaceutically acceptable solvent, such as water for injection or Na2HPO4 in water for injection. After complexation of the statin, the pH may be adjusted to a pH of over 6.5. In certain embodiments the pH is modified to from about 7 to about 9. Suitable agents for modifying the pH include sodium phosphate buffer (either sodium phosphate tribasic ($Na_3PO_4$) or sodium phosphate dibasic ($Na_2HPO_4$)), o-phosphoric acid, NaOH and L-Arginine (L-dArg).

In certain embodiments of the present invention, the mixture is mixed by a variety of means including vortexing and sonication. The mixing may be repeated more than 1 time. It may be desirable to adjust the volume of solution and/or its pH between each mixing step.

In an embodiment of the invention, the mixture of statin and complexing agent is lyophilized.

The stability of the formulations of the present invention is determined by any suitable method known to those of skill in the art. An example of a suitable method of testing stability is using high performance liquid chromatography or other common analytical technology.

The daily dose of active ingredient can administered as a single dose. The dosage regimen and administration frequency for treating the mentioned diseases with the compound of the invention and/or with the pharmaceutical compositions of the present invention will be selected in accordance with a variety of factors, including for example age, body weight, sex and medical condition of the patient as well as severity of the disease, pharmacological considerations, half-life of the drug, and eventual concomitant therapy with other drugs. In some instances, dosage levels below or above the aforesaid range and/or more frequent may be adequate, and this logically will be within the judgment of the physician and will depend on the disease state.

Where the active ingredient is atorvastatin, the total daily dose may be in amounts preferably from 10 to 80 mg but may be lower or higher as required. The preferable starting dose of atorvastatin is 10 or 20 mg once daily, though if needed large LDL-C reduction may start at 40 mg once daily. The pediatric starting dose of atorvastatin is 10 mg once daily with a maximum does of 20 mg once daily. For HMG CoA reductase inhibitors other than atorvastatin, it is within the understanding of one of skill in the art to calculate conversion dosing based on the preferable dosing for atorvastatin. In addition, conversion tables for such calculation are readily available for many of the known statins.

The compounds of the invention may be administered orally, parenterally, rectally or topically, by inhalation or aerosol, in formulations eventually containing conventional non-toxic pharmaceutically acceptable carriers, adjuvants and vehicles as desired. Topical administration may also involve the use of transdermal administration such as transdermal patches or iontophoresis devices. The term "parenteral" as used herein, includes subcutaneous injections, intravenous, intramuscular, intrasternal injection or infusion techniques.

Injectable preparations, for example sterile injectable aqueous or oleaginous suspensions may be formulated according to known art using suitable dispersing or wetting agents and suspending agents. The sterile injectable preparation may also be a sterile injectable solution or suspension in a non-toxic parenterally acceptable diluent or solvent. Among the acceptable vehicles and solvents are water, Ringer's solution and isotonic sodium chloride. In addition, sterile, fixed oils are conventionally employed as a solvent or suspending medium. For this purpose any bland fixed oil may be employed including synthetic mono or diglycerides, in addition fatty acids such as oleic acid find use in the preparation of injectables.

Liquid dosage forms for oral administration may include pharmaceutically acceptable emulsions, solutions, suspensions, syrups and elixirs containing inert diluents commonly used in the art, such as water. Such compositions may also comprise adjuvants, such as wetting agents, emulsifying and suspending agents, and sweetening, flavoring and the like.

Newer statin nitroderivatives in addition to lowering lipid, possess enhanced anti-inflammatory, antiplatelet and antithrombotic effects as compared to native statins. Moreover, they can be effective also in the other pathologies such as acute coronary syndromes, stroke, peripheral vascular diseases such as peripheral ischemia, all disorders associated with endothelial dysfunctions such as vascular complications in diabetic patients and atherosclerosis, neurodegenerative diseases such as Alzheimer's disease (AD) and Parkinson's disease (PD), autoimmune diseases such as multiple sclerosis.

In alternative embodiments of the treatment methods described herein, a pharmaceutical formulation comprising a statin is administered to a patient via an injection method. In such embodiments the pharmaceutical formulation of the statin is a formulation suitable for administration to a patient via the injection method. Suitable injection methods include, in addition to intravenous injection, intraarterial infusion, intramuscular injection, transdermal injection, and subcutaneous injection.

Suitable carriers for intravenous administration include physiological saline or phosphate buffered saline (PBS), and solutions containing solubilizing agents, such as glucose, polyethylene glycol, and polypropylene glycol and mixtures thereof.

The formulation may include an aqueous vehicle. Aqueous vehicles include, by way of example and without limitation, Sodium Chloride Injection, Ringers Injection, Isotonic Dextrose Injection, Sterile Water Injection, Dextrose, and Lactated Ringers Injection. Nonaqueous parenteral vehicles include, by way of example and without limitation, fixed oils of vegetable origin, cottonseed oil, corn oil, sesame oil and peanut oil. Antimicrobial agents in bacteriostatic or fungistatic concentrations must be added to parenteral preparations packaged in multiple dose containers which include phenols or cresols, mercurials, benzyl alcohol, chlorobutanol, methyl and propyl p hydroxybenzoic acid esters, thimerosal, benzalkonium chloride and benzethonium chloride. Isotonic agents include, by way of example and without limitation, sodium chloride and dextrose. Buffers include phosphate and citrate. Antioxidants include sodium bisulfate. Local anesthetics include procaine hydrochloride. Suspending and dispersing agents include sodium carboxymethylcelluo se, hydroxypropyl methylcellulose and polyvinylpyrrolidone. Emulsifying agents include Polysorbate 80 (TWEEN® 80) A sequestering or chelating agent of metal ions include EDTA.] Pharmaceutical carriers also include, by way of example and without limitation, ethyl alcohol, polyethylene glycol and propylene glycol for water miscible vehicles and sodium hydroxide, hydrochloric acid, citric acid or lactic acid for pH adjustment.

Typically a therapeutically effective dosage is formulated to contain a concentration of at least about 0.1% w/w up to about 90% w/w or more, such as more than 1% w/w of the statin. In certain embodiments, the solubilized statin concentration of the formulation will be at least about 3.3 mg/ml.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

In certain embodiments, the invention is directed to a method of reducing the risk of MI, stroke, revascularization procedures, angina in patients without CHD but with multiple risk factors, reducing the risk of MI and stroke in patients with type 2 diabetes without CHD, but with multiple risk factors, reducing the risk of non-fatal MI, fatal and non-fatal stroke, revascularization procedures, hospitalization for CHF, and angina in patients with CHD, reducing elevated total-cholesterol, LDL-cholesterol, apolipoprotein-B, and triglyceride levels in patients with primary hyperlipidemia (heterozygous familial and nonfamilial and mixed dyslipidemia), reducing elevated triglyceride levels in patients with hypertriglyceridemia and primary dysbetalipoproteinemia, reducing total cholesterol and LDL-cholesterol in patients with homozygous familial hypercholesterolemia, reducing elevated total-C, LDL-C, and apo B levels in boys and postmenarchal girls, 10 to 17 years of age, with heterozygous familial hypercholesterolemia after failing an adequate trial of diet therapy, mixed dyslipidaemia; and heterozygous familial hyperlipidemia, homozygous familial hypercholesterolaemia as an adjunct to other lipid-lowering treatments (e.g. LDL apheresis) or if such treatments are unavailable.

Particularly, the non-statin pharmaceutical drugs for use in the practice of this invention are any of the PPAR receptor agonists, including those that are selective for one PPAR receptor sub-type as well as those that are active for two or more receptor sub-types. More particularly, the non-statin pharmaceutical drugs are PPAR alpha agonists such as the fibric acid derivatives; PPAR gamma agonists; and dual PPAR alpha/gamma agonists, i.e., those having dual activity for both the alpha and the gamma receptor sub-types.

When a statin and a non-statin are referred to as competitively binding to an enzyme or enzyme isoform (i.e., isozyme), it means both the statin and the non-statin bind to the same enzyme or isozyme. An adverse pharmacokinetic drug interaction is intended to mean an in vivo interaction between a statin and a co-administered non-statin pharmaceutical drug in a mammal, particularly a human, which raises the plasma level of active open-acid statin above the level it would be at if the statin was administered alone, i.e., absent the co-administered non-statin.

DETAILED DESCRIPTION OF THE PREFERRED EMBODIMENTS

The following examples illustrate various aspects of the present invention. They are not to be construed to limit the claims in any manner whatsoever.

Examples 1-3

Examples 1-3 compare solubilization methods to evaluate the affect of pH, buffer strength, and different mixing methods. In Example 1, samples were made in 100 mM sodium phosphate dibasic ($Na_2HPO_4$) at pH 5.5, 6.5, 7.5, and 8.5. The samples were only vortexed. In Example 2, samples were made in 100 mM Na2HPO4 at pH 5.5, 6.5, 7.5, and 8.5 and then both vortexed and sonicated. In Example 3, samples were made in either 25 or 50 mM $Na_2HPO_4$ at either pH 7.5 or 8.5.

Example 1

10 mg of atorvastatin calcium trihydrate ("AS-Ca") was added to approximately 0.9 mls of a solution containing 0.8 mls of 34.7% hydroxy-propyl-β-cyclodextrin ("HPβ-CD") and 0.1 ml of 1 M Na2HPO4 in ultrapure water and then vortexed at top speed for 5 minutes. The pH of the samples were then adjusted to pH 5.5, 6.5, 7.5, or 8.5 with 0.85% o-phosphoric acid or 0.1 M NaOH. Each sample was vortexed, and then ultra-pure water was added to q.s. to 1.0 mls, after which the sample was filtered through a 0.45 μm nylon filter, and analyzed by HPLC (see Table 1).

Example 2

The formulations of Example 2 were prepared in the same manner as those of Example 1, except that after vortexing, the formulations of Example 2 were additionally sonicated. The samples were analyzed by HPLC (See Table 1).

Example 3

10 mg of AS-Ca was added to approximately 0.9 mls of a solution containing 0.8 mls of 34.7% HPβ-CD and either 0.025 or 0.050 ml of 1 M $Na_2HPO_4$ in ultrapure water and then vortexed for 5 min. The pH of the samples was adjusted to either 7.5 or 8.5 using 0.1 M NaOH, and then ultrapure water was added q.s. to 1 mL, after which the samples were vortexed for 5 min, filtered, and then analyzed by HPLC (See Table 1).

TABLE 1

| Example | Sample pH | Na2HPO4 concentration (mM) | Mixing Method | Solubilized Atorvastatin (mg/ml) |
|---|---|---|---|---|
| 1 | 5.5 | 100 | Vortex | 3.32 |
|   | 6.5 | 100 | Vortex | 8.42 |
|   | 7.5 | 100 | Vortex | 8.89 |
|   | 8.5 | 100 | Vortex | 7.97 |
| 2 | 5.5 | 100 | Sonication | 3.27 |
|   | 6.5 | 100 | Sonication | 9.21 |
|   | 7.5 | 100 | Sonication | 9.06 |
|   | 8.5 | 100 | Sonication | 9.26 |
| 3 | 7.5 | 25 | Vortex | 8.34 |
|   | 7.5 | 50 | Vortex | 8.58 |
|   | 8.5 | 25 | Vortex | 9.26 |
|   | 8.5 | 50 | Vortex | 9.65 |

Results:
The solubility of AS-Ca was greatly improved by adjusting the pH to 6.5 and above.

Examples 4-5

The solubility of AS-Ca in formulations using different methods of pH adjustment are compared in Examples 4 and 5 to evaluate complexation efficiency. In Example 4, the pH was adjusted to 9 using NaOH and then phosphoric acid was added to reduce the pH back to pH 7.0-8.5. In Example 5, the pH was adjusted to a pH between 7.0-8.5 with either 0.85% o-phosphoric acid or 0.1 M NaOH.

Example 4

Mixtures of 20 mg/ml of AS-Ca were prepared by adding 20 mg AS-Ca to approximately 0.8 mL mixture of 27.78% HPβ-CD, 50 mM $Na_2HPO_4$, and ultrapure water and then phosphoric acid and/or NaOH were added to q.s. to 1 ml. The mixture of 20 mg/ml AS-Ca was then vortexed for 5 min and sonicated for 15 minutes.

The pH of the samples were adjusted to pH 9.0 using 0.1 M NaOH after which the pH was further adjusted to pH 7.0, 7.5, 8.0, or 8.5 with 0.85% o-phosphoric acid. Each sample was vortexed, q.s. to 1.0 mls with ultra-pure water, filtered, and then analyzed by HPLC.

Example 5

Mixtures of 20 mg/ml of AS-Ca was prepared by adding 20 mg AS-Ca to approximately 0.8 ml mixture of 27.78% HPβ-CD, 50 mM Na2HPO4, and ultrapure water and then phosphoric acid and/or NaOH were added to q.s. to 1 ml. The mixture of 20 mg/ml AS-Ca was then vortexed for 5 min and sonicated for 15 minutes.

The pH of the samples were adjusted to pH 7.0, 7.5, 8.0, or 8.5 with either 0.85% o-phosphoric acid or 0.1 M NaOH. Each sample was vortexed, q.s. to 1.0 mls with ultra-pure water, filtered, and then analyzed by HPLC.

Results: Results are provided below in Table 2.

TABLE 2

| Example | Sample pH | Atorvastatin Concentration mg/ml |
|---|---|---|
| 4 | 7.0 | 18.45 |
|   | 7.5 | 17.90 |
|   | 8.0 | 19.62 |
|   | 8.5 | 18.51 |
| 5 | 7.0 | 16.93 |
|   | 7.5 | 17.83 |
|   | 8.0 | 18.97 |
|   | 8.5 | 19.44 |

Example 6

The relationship between AS-Ca and HPβ-CD was examined by evaluating the complexation efficiency of different concentrations of HPβ-CD. A stock solution of HPβ-CD was first prepared at 34.7% and serially diluted to 0.5375% HPβ-CD.

Samples were prepared by adding 20 mg of AS-Ca to 0.8 mls of HPβ-CD dilutions (final concentration in 1 ml from 27.78% to 0.5375% HPβ-CD) and 0.05 ml of 1 M $Na_2HPO_4$. Each sample was adjusted to pH 9.0 with 0.1 M NaOH and then the samples were vortexed for 5 minutes and then sonicated for 15 minutes. The pH was then adjusted to either 7.5 or 8.5 with 0.85% o-phosphoric acid. The samples were vortexed and sonicated again, then filtered and analyzed by HPLC (see Table 3).

Figure 1:
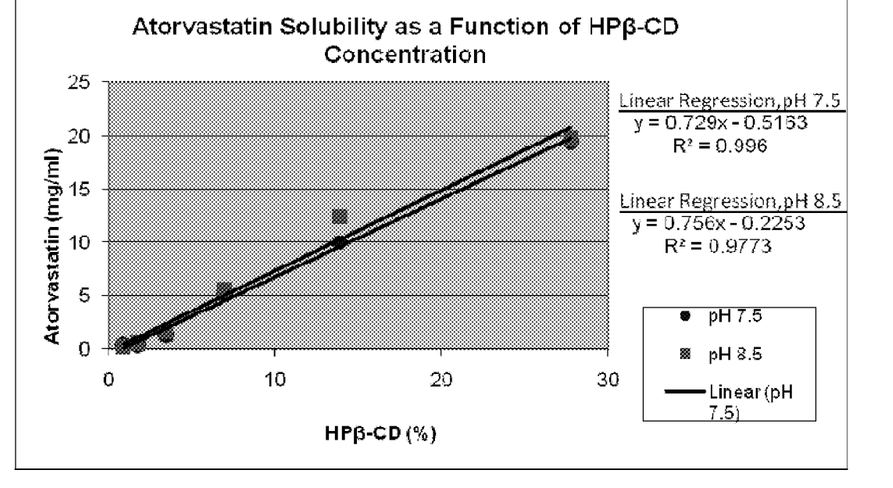
FIG. 1 is shows a linear regression analysis of the minimum amount of HPβ-CD needed to solubilize AS-Ca.

Results: The solubility of AS-Ca increased linearly with HPβ-CD concentration. Linear regression analysis showed that the minimum amount of HPβ-CD needed to solubilize AS-Ca at 10 mg/ml was 14.4% at pH 7.5 and 13.5% at pH 8.5. (See FIG. 1).

TABLE 3

| pH 7.5 | | pH 8.5 | |
| --- | --- | --- | --- |
| HPβ-CD (%) | Atorvastatin (mg/ml) | HPβ-CD (%) | Atorvastatin Concentration (mg/ml) |
| 27.78 | 19.48 | 27.78 | 19.72 |
| 13.89 | 10.01 | 13.89 | 12.42 |
| 6.94 | 5.13 | 6.94 | 5.54 |
| 3.47 | 1.38 | 3.47 | 1.58 |
| 1.74 | 0.43 | 1.74 | 0.52 |
| 0.87 | 0.34 | 0.87 | 0.215 |

Example 7

Forced degradation and preliminary stability studies showed that AS-Ca solubilized with HPβ-CD did not exhibit good stability. Therefore, lyophilization was evaluated using a manifold freeze dryer to determine whether stability could be improved by this method.

100 mg of AS-Ca was added to approximately 9 mls of a solution containing 5.333 ml of 37.5% HPβ-CD and 0.5 ml of 1 M $Na_2HPO_4$. The sample was vortexed for 5 minutes and then sonicated for 15 minutes. The pH was then adjusted to 9.0 using 0.1M NaOH, after which the sample was again vortexed and sonicated.

Next, the pH of the sample was adjusted to pH 8.5 using 0.85% o-phosphoric acid followed by vortexing and sonication. The sample was q.s. to 10 mls with NaOH and 1% phosphoric acid to a pH of 8.47, filtered and then analyzed by HPLC. The final formulation contained 10 mg/ml AS-Ca2+, 20% HPβ-CD, 50 mM $Na_2HPO_4$, q.s. with 0.1 M NaOH and 1% phosphoric acid at a pH of 8.47.

Results: AS-Ca solubilized with HPβ-CD was lyophilized and then placed on stability at 40° C. for 1 month alongside a control solution of the same mixture. Lyophilized AS-Ca degraded ~3.5% and AS-Ca in solution degraded ~15.5%. Therefore, the sample was not stable in solution or when lyophilized using a manifold freeze-dryer.

Example 8

Atorvastatin was prepared as described in example 6, except it was prepared at 20 mg/mL in 30% HPβ-CD in 100 mM sodium phosphate adjusted to a final pH of 8.5. The sample was then diluted 1:1 into an 8% sucrose solution and transferred to 5 mL vials. The vials were capped with lyophilization stoppers.

The samples were frozen at −40° C. on a shelf freezer followed by a 60 min hold. After the freezing step, the condenser was adjusted to −85° C. and held at that temperature throughout the run. The pressure was approximately 20 mtorr. The shelf temperature was then adjusted to −20° C., −10° C., and 0° C. and held for 180 min at each temperature while maintaining vacuum. Next the temperature was ramped to 10° C. and then to 20° C. (240 minutes for each step). The temperature was then adjusted to 40° C. and held until the vacuum was released and vials removed and visually inspected.

Results: When AS-Ca was solubilized with HPβ-CD and then lyophilized using a shelf freeze dryer, no degradation (less than 0.1%) was observed after storage for 1 month at 40° C. Although not wishing to be bound by this theory, the enhanced stability is likely due to rapid removal of water and low residual moisture levels obtained by conditions of the lyophilization cycle.

Examples 9 and 10

In Examples 9 and 10, Sulfobutyl-ether-β-cyclodextrin ("SBE-β-CD") was evaluated as a possible alternative to HPβ-CD by means of AS-Ca complexation with SBE-β-CD. The effect of sodium phosphate salt versus ultrapure water on the solubilization of AS-Ca with SBE-β-CD at different pH was also evaluated.

Example 9

In Example 9, AS-Ca complexation with SBE-β-CD was in sodium phosphate buffers with different pH values. 20 mg/ml of AS-Ca was added into 27.78% SBE-β-CD in 50-100 mM of either $NaH_2PO_4$ (pH 2.13 samples) or $Na_2HPO_4$ (pH 7.07, 8.75, and 11.75 samples). Each sample was then vortexed and sonicated, after which the pH was adjusted to 2.13 and 7.07 using 0.85% o-phosphoric acid or 8.75 and 11.50 with 0.1 M NaOH. The samples were then vortexed, sonicated, q.s. to 1.0 ml with ultrapure water, and then filtered and analyzed by HPLC (see Table 4 below).

Results: The solubility of AS-Ca was roughly 10-fold lower when complexed with SBE-β-CD than when complexed with HPβ-CD.

TABLE 4

| Sample pH | Atorvastatin (mg/ml) |
| --- | --- |
| 2.13 | 0.228 |
| 7.07 | 1.993 |
| 8.75 | 1.267 |
| 11.75 | 1.927 |

Example 10

In Example 10, the AS-Ca complexation with SBE-β-CD was in ultrapure water to investigate the impact of phosphate buffer salt on the ability of SBE-β-CD to complex AS-Ca. Based on the solubility findings of Example 8, the formulation was tried at neutral and basic pH.

Neutral pH: 20 mg/ml AS-Ca was added to 27.78% SBE-β-CD in ultrapure water. The sample was vortexed and sonicated, after which the pH determined to be 7.09. The sample was then q.s. to 1.0 ml with ultrapure water, filtered, and analyzed by HPLC. (See Table 5)

Basic pH: 20 mg/ml AS-Ca was added to 27.78% SBE-β-CD in approximately 0.8 mL ultrapure water. The sample was processed as described above, except the pH was adjusted to 11.0 using 0.1 M NaOH and q.s. to 1.0 mL.

Results: Phosphate buffer does not appear to have a significant effect on the solubility of atorvastatin combined with SBE-β-CD.

TABLE 5

| Sample pH | Atorvastatin (mg/ml) |
|---|---|
| 7.09 | 1.392 |
| 11.0 | 1.927 |

Example 11

Additional AS-Ca formulations were prepared using other cyclodextrins, including γ-cyclodextrin and hydroxyl-propyl-γ-cyclodextrin. The solubility was found to be less than that achieved with SBE-β-CD or HPβ-CD.

Example 12

In Example 12, the AS-Ca was solubilized with a co-solvent to evaluate co-solvent/aqueous solubility as a function of pH. The pH dependence on propylene glycol and ethanol co-solvent formulations was, in particular, examined.

10 mg of AS-Ca was added to approximately 0.9 mls of solution containing 4.0 mls of propylene glycol and 1.0 ml of ethanol in ultrapure water. The sample was vortexed and sonicated as described above, then adjusted to pH 9.0 with 0.1 M NaOH. The samples were vortexed and sonicated again and then the pH was adjusted to pH 7.0, 7.5, 8.0, or 8.5 with 0.85% o-phosphoric acid or left at pH 9.0. The samples were vortexed, sonicated, the sample was q.s. to 1.0 ml with ultrapure water, filtered, and then analyzed by HPLC. (See Table 6)

Results: There was no difference in solubility when pH was varied from 7.0 to 9.0. However, when the samples were diluted 1:1 into water, the samples adjusted to pH 7.5 and 8.0 precipitated. Therefore, a pH>8.0 is preferable when the product is to be diluted in aqueous vehicles.

TABLE 6

| Sample pH | Atorvastatin (mg/ml) |
|---|---|
| 9.00 | 9.280 |
| 8.50 | 9.506 |
| 8.00 | 8.641 |
| 7.50 | 9.361 |
| 7.00 | 8.876 |

Example 13

Example 13 examines the amount of solvent needed to solubilize AS-Ca by evaluating co-solvent/aqueous solubility as a function of co-solvent proportions.

10 mg of atorvastatin calcium was added to approximately 0.9 mls of solution containing the following solvent ratios in ultrapure water:

a. 40/10, 4.0 mls of propylene glycol and 1.0 ml of ethanol
b. 30/10, 3.0 mls of propylene glycol and 1.0 ml of ethanol
c. 20/10, 2.0 mls of propylene glycol and 1.0 ml of ethanol
d. 40/5, 4.0 mls of propylene glycol and 0.5 ml of ethanol
e. 40/0, 4.0 mls of propylene glycol and 0.0 ml of ethanol The samples were each vortexed for 5 min and then sonicated for 15 minutes. The samples were first adjusted to pH 9.00 with 0.1 M NaOH, vortexed, and then sonicated. The pH of the samples was adjusted to pH 8.50 with 0.85% o-phosphoric acid and the samples were again vortexed and sonicated. The samples were q.s. to 1.0 ml with ultrapure water, filtered, and then analyzed by HPLC (see Table 7).

Results: The best solubility was achieved with 40% propylene glycol (v/v) and 10% ethanol (v/v). Forced degradation studies showed that anything less than 40% propylene glycol and 10% ethanol resulted in atorvastatin precipitation when diluted with normal saline.

TABLE 7

| Sample | PG/EtOH | Concentration mg/ml |
|---|---|---|
| A | 40/10 | 21.27 |
| B | 30/10 | 17.87 |
| C | 20/10 | 16.80 |
| D | 40/5 | 18.11 |
| E | 40/0 | 16.06 |

Example 14

Forced degradation studies also showed significant degradation with co-solvent/aqueous vehicles. Therefore, non-aqueous co-solvents were examined.

10 mg of AS-Ca was added to a 1.0 ml of propylene glycol and ethanol (4/1). The samples were vortexed and then the pH of the sample was adjusted to pH 11.0 with 0.1 M NaOH. The samples were then filtered, and analyzed by HPLC.

Results: The sample was completely soluble (9.34 mg/ml). When the solution was diluted 1:3 in saline, it precipitated.

Example 15

Forced degradation analysis showed that AS-Ca was relatively stable at high pH. Therefore, the pH was adjusted with L-Arginine (L-Arg), NaOH, or sodium phosphate buffer (either sodium phosphate tribasic ($Na_3PO_4$) or $Na_2HPO_4$).

20 mg of AS-Ca was added to approximately 0.8 mL ml of the solutions 1-5 below, followed by vortexing and sonication. The pH of the samples was adjusted to a basic pH followed by q.s. to a volume of 1 mL with ultrapure water, vortexing, sonication, filtering, and HPLC analysis.

Solution 1: 20 mg of AS-Ca was added to water containing 16.54 mM L-Arg (1:1 Atorvastatin:L-Arg molar ratio). The pH was adjusted to 10.98 with 10% L-Arg. The resulting AS-Ca concentration was 0.46 mg/ml.

Solution 2: 20 mg of AS-Ca was added to water and the pH was adjusted to 11.68 with 0.1 M NaOH. The resulting AS-Ca concentration was 0.222 mg/ml.

Solution 3: 20 mg AS-Ca was added to water containing 0.1 M $Na_3PO_4$. The measured pH was 11.75. The resulting AS-Ca concentration was 0.46 mg/ml.

Solution 4: 20 mg of AS-Ca was added to water containing 0.1 M $Na_3PO_4$ and 16.54 mM L-Arg. The measured pH was pH 10.79. The resulting AS-Ca concentration was 3.17 mg/ml.

Solution 5: 20 mg AS-Ca was added to water containing 0.1 M $Na_2HPO_4$ and 16.54 mM L-Arg. The measured pH was 10.79. The resulting AS-Ca concentration was 3.43 mg/ml.
Results: The solubility of AS-Ca in basic solutions with no HPβ-CD varied from ~0.2 to 3.5 mg/mL. Using 16.54 mM L-Arg with either 0.1 M $Na_3PO_4$ or $Na_2HPO_4$ resulted in AS-Ca concentrations of >3 mg/mL. Therefore using a combination of L-Arg with either $Na_3PO_4$ or $Na_2HPO_4$ also provides adequate solubility for preparation of AS-Ca in solutions.

Examples 16-19

Atorvastatin free acid solubility ("AS") was examined as an alternative to the calcium trihydrate version.

Example 16

The solubility of AS with complexation was evaluated by examining the solubility of AS-Ca in 27.78% of either HPβ-CD or SBE-β-CD in 50 mM $Na_2HPO_4$ adjusted to pH 10.35 and 10.65 using 0.1 M NaOH respectively. The same methods of solubilization were used as example 4.
Results: AS solubility was 13.3 mg/ml with HPβ-CD and 1.96 mg/ml with SBE-β-CD complexation.

Example 17

In Example 17, solubilization of AS with a co-solvent was evaluated by testing whether AS could be dissolved in a non-aqueous co-solvent at high pH and then diluted into saline, without precipitation. Previous data (example 13) showed that the AS-Ca would precipitate when prepared in non-aqueous co-solvents and then diluted into saline.
20 mg AS (20 mg) was added to approximately 0.9 mls of propylene glycol and ethanol (4/1 ratio) co-solvent. The measured pH was 6.64. The pH was adjusted to pH 11.0 with 0.1 M NaOH, q.s. to a volume of 1 mL with ultrapure water. The sample was then vortexed, filtered, after which it was analyzed by HPLC.
Results: The sample degraded rapidly (approximately 50% in 2 hours). The peak area was conserved between atorvastatin and its degradation peaks. The AS concentration was estimated to be about 20 mg/ml.

Example 18

In Example 18, AS solubility in either 100% propylene glycol or 100% ethanol similar to the propylene glycol/ethanol (4/1) solvent using the same methods of solubilization described above. Atorvastatin free acid was completely soluble in either 100% propylene glycol or 100% ethanol similar to the propylene glycol/ethanol (4/1) solvent. Both solutions precipitated when diluted 1:1 with saline and were found to be unstable.

Example 19

In Example 19, the solubility of AS was examined by adjusting to a high pH with L-Arginine (L-Arg), NaOH, or sodium phosphate buffer (either ($Na_3PO_4$) or $Na_2HPO_4$).
20 mg of AS was added to approximately 0.8 ml of the solutions below followed by vortexing and sonication. The pH of the samples was adjusted to a basic pH, followed by q.s. to a volume of 1 mL with ultrapure water. The sample was then vortexed, sonicated, filtered, and HPLC analysis was conducted.

Sample 1: 20 mg AS was added to a solution of 16.54 mM L-Arg. The measured pH was 10.35, which was then adjusted to 10.71 with L-Arg. The resulting AS-Ca concentration was 1.91 mg/ml.
Sample 2: 20 mg AS was added to ultrapure water and the pH was adjusted to 11.15 with 0.1 M NaOH. The resulting AS concentration was 0.06 mg/ml.
Sample 3: 20 mg AS was added to 16.54 mM L-Arg and 0.1M Na3PO4. The measured pH was 11.42. The resulting AS concentration was 0.44 mg/ml
Sample 4: 20 mg AS was added to 0.05 M $Na_3PO_4$. The measured pH was 11.55. The resulting AS concentration was <LOQ (Limit of Quantitation).

Non-aqueous formulations composed of propylene glycol/ethanol (4/1) at pH 11.0 were examined to decrease the observed degradation. However, that formulation precipitated when diluted 1:1 into normal saline. To improve stability, preliminary lyophilized formulations of AS-Ca with HPβ-CD were examined. Initial stability of this formulation showed improved stability over leaving the sample in solution.

It will be readily apparent to one of ordinary skill in the relevant arts that other suitable modifications and adaptations to the methods and applications described herein are suitable and may be made without departing from the scope of the invention or any embodiment thereof. While the invention has been described in connection with certain embodiments, it is not intended to limit the invention to the particular forms set forth, but on the contrary, it is intended to cover such alternatives, modifications and equivalents as may be included within the spirit and scope of the invention as defined by the following claims.
Results: The solubility of AS in basic solutions using $Na_3PO_4$, NaOH, or $Na_3PO_4$ and L-Arg was <1.0 mg/mL. ASs solubility was 1.91 mg/mL when using L-Arg alone. Therefore using L-Arg at an elevated pH provides an adequate solubility.

We claim:
1. A pharmaceutical formulation comprising an effective amount of atorvastatin or a pharmaceutically acceptable salt thereof complexed with a sufficient amount of a pharmaceutically acceptable complexing agent which is hydroxy-propyl-β-cyclodextrin in an aqueous solution having a pH of from about 5.5 to about 11 such that said atorvastatin is solubilized without precipitate and the concentration of said atorvastatin in solution is from about 3.32 mg/ml to about 25 mg/ml.
2. The formulation claim 1, wherein the complexing agent comprises at least 13.5% of the formulation.
3. The formulation of claim 1, wherein the solubilized statin concentration is from about 5 to about 15 mg/ml.
4. The formulation of claim 1, wherein the solubilized statin concentration is about 10 mg/ml.
5. A method of preparing a formulation of a pharmaceutically acceptable product comprising:
   (a) adding atorvastatin or a pharmaceutically acceptable salt thereof to a mixture of a pharmaceutically acceptable complexing agent which is hydroxy-propyl-β-cyclodextrin and a suitable solvent to solubilize the atorvastatin without precipitate and provide a concentration of atorvastatin in solution from about 3.32 mg/ml to about 25 mg/ml;
   (b) mixing; and
   (c) adjusting the pH of the mixture using a pharmaceutically acceptable buffer, an alkalizing agent, or a combination of a pharmaceutically acceptable buffer and an alkalizing agent in an amount sufficient to provide a pH range from about 5.5 to about 11.

6. The method of claim 5, wherein the complexing agent comprises at least 13.5% of the formulation.

7. The method of claim 5, wherein the pharmaceutically acceptable buffer is a sodium phosphate buffer.

8. The method of claim 5, wherein the pharmaceutically acceptable buffer is $Na_2HPO_4$.

9. A parenteral pharmaceutical formulation which is an aqueous solution suitable for injection comprising an effective amount of a pharmaceutically acceptable water insoluble statin which is atorvastatin calcium complexed with a sufficient amount of a pharmaceutically acceptable complexing agent which is hydroxy-propyl-β-cyclodextrin to solubilize the atorvastatin without precipitate in an aqueous solution suitable for injection, the aqueous solution suitable for injection further comprising either a pharmaceutically acceptable buffer, or an alkalizing agent, or a combination of a pharmaceutically acceptable buffer and an alkalizing agent, in an amount sufficient to provide a pH of from about 5.5 to about 11 and the concentration of said atorvastatin in solution is from about 3.32 mg/ml to about 25 mg/ml.

10. The formulation of claim 9, wherein the pharmaceutically acceptable buffer is $Na_2HPO_4$.

11. The formulation of claim 9, wherein the solubilized statin concentration is from about 5 to about 15 mg/ml.

12. The formulation of claim 9, wherein the solubilized statin concentration is about 10 mg/ml.

13. The formulation of claim 9, which includes a dose of atorvastatin from about 10 mg to about 80 mg.

14. The formulation of claim 9, wherein the pharmaceutically acceptable buffer is a phosphate buffer.

15. The formulation of claim 9, wherein the pharmaceutically acceptable buffer or alkalizing agent is NaOH, KOH, triethylamine, meglumine, L-Arginine, sodium phosphate buffer, sodium bicarbonate, and mixtures of any of the foregoing.

16. The formulation of claim 9, wherein the aqueous solution suitable for injection has a pH from about 7 to about 9.

17. The formulation claim 9, wherein the complexing agent comprises at least 13.5% of the formulation.

18. The formulation of claim 1, wherein the aqueous solution has a pH from about 7 to about 9.

19. The formulation of claim 9, wherein the aqueous solution suitable for injection contains a pharmaceutically acceptable buffer or alkalizing agent selected from the group consisting of NaOH, KOH, triethylamine, meglumine, L-Arginine, sodium phosphate buffer, sodium bicarbonate, and mixtures of any of the foregoing.

20. The formulation of claim 19, wherein the aqueous solution has a pH from about 7 to about 9.

21. The formulation of claim 1, further comprising either a pharmaceutically acceptable buffer, or an alkalizing agent, or a combination of a pharmaceutically acceptable buffer and an alkalizing agent in an amount sufficient to provide a pH of from about 5.5 to about 11 and a solubilized atorvastatin concentration from about 5 mg/ml to about 25 mg/ml.

22. The formulation of claim 21, wherein the buffer comprises a sodium phosphate buffer or a sodium bicarbonate buffer.

23. The formulation of claim 21, wherein the alkalizing agent is NaOH, KOH, triethylamine, meglumine, or L-Arginine.

24. The formulation of claim 1, wherein the atorvastatin is atorvastatin calcium trihydrate.

25. The formulation of claim 21, which has a solubilized atorvastatin concentration from about 10 mg/ml to about 25 mg/ml.

26. The formulation of claim 9, which has a solubilized atorvastatin concentration from about 10 mg/ml to about 15 mg/ml.

27. The method of claim 5, wherein the concentration of atorvastatin in solution is from about 10 mg/ml to about 25 mg/ml.

* * * * *